US012765848B2

(12) United States Patent
Vija et al.

(10) Patent No.: US 12,765,848 B2
(45) Date of Patent: Oct. 20, 2026

(54) SMALL FOOTPRINT MULTI-USE SPECT SYSTEM

(71) Applicant: Siemens Medical Solutions USA, Inc., Malvern, PA (US)

(72) Inventors: Alexander Hans Vija, Evanston, IL (US); Miesher Rodrigues, Buffalo Grove, IL (US); Dennis Steibel, Lake Zurich, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 225 days.

(21) Appl. No.: 18/696,527

(22) PCT Filed: Dec. 1, 2021

(86) PCT No.: PCT/US2021/072656
§ 371 (c)(1),
(2) Date: Mar. 28, 2024

(87) PCT Pub. No.: WO2023/101703
PCT Pub. Date: Jun. 8, 2023

(65) Prior Publication Data

US 2024/0389957 A1 Nov. 28, 2024

(51) Int. Cl.
*A61B 6/03* (2006.01)
*A61B 6/00* (2024.01)
*A61B 6/46* (2024.01)

(52) U.S. Cl.
CPC ............ *A61B 6/037* (2013.01); *A61B 6/4458* (2013.01); *A61B 6/469* (2013.01); *A61B 6/5241* (2013.01)

(58) Field of Classification Search
CPC ........... A61B 6/06; A61B 6/547; A61B 6/488; A61B 6/037; A61B 6/5241; A61B 6/469;
(Continued)

(56) References Cited

U.S. PATENT DOCUMENTS 4,859,852 A * 8/1989 Genna .................... G21K 1/025 250/363.1
5,324,946 A * 6/1994 Ichihara ................ G01T 1/2985 250/363.04
(Continued)

FOREIGN PATENT DOCUMENTS

DE 102008034579 A1 2/2010
JP H09251078 9/1997
(Continued)

OTHER PUBLICATIONS

"Mobile SPECT Imaging and Gamma Camera Solution on a Small Footprint", SURGICeye, Aug. 3, 2021, https://www.surgiceye.com/fo-healthcare-professionals/declipsespect-imaging-probe/, (pp. 1-6, 6 total pages).
(Continued)

*Primary Examiner* — Irakli Kiknadze

(57) ABSTRACT

A system and method include generation of a first tomographic image of a subject based on first gamma rays detected by the detector while the detector is disposed at a first position with respect to the subject, generation of a second tomographic image of the subject based on second gamma rays detected by the detector while the detector is disposed at a second position with respect to the subject, identification of one or more structures of the subject depicted in the first tomographic image and the second tomographic image, and generation of a composite tomographic image based on the first tomographic image, the second tomographic image, and the identified one or more structures.

16 Claims, 12 Drawing Sheets

(58) Field of Classification Search

CPC ..... A61B 6/4458; A61B 6/5217; A61B 6/503; A61B 6/501; A61B 90/36; A61B 6/507; A61B 2090/364; A61B 34/10; A61B 2090/374; A61B 6/025; A61B 6/03; A61B 6/4441; A61B 6/461; A61B 6/465; A61B 6/467; A61B 6/463; A61B 6/4405; A61B 6/487; A61B 6/0492; A61B 6/502; A61B 6/5294; A61B 6/5264; A61B 6/032; A61B 6/5205; A61B 5/704; A61B 90/06; A61B 34/20; A61B 6/5235; A61B 6/4266; A61B 6/4258; A61B 8/4254; A61B 6/4417; A61B 90/50; A61B 6/4291; A61B 8/4416; A61B 8/4218; A61B 8/485; A61B 6/12; A61B 8/4227; A61B 8/4477; A61B 6/5247; A61B 6/466; A61B 6/486; A61B 6/548; G01T 7/00; G01T 1/1647; G01T 1/1642; G01T 1/1648; G01T 1/1641; G01T 1/2985; G01T 1/00; G01T 1/295; G01T 1/1644; G01T 1/1603; G21K 1/02; G21K 1/025; G06T 11/008; G06T 11/005; G06T 2210/41; G06T 2211/424; G06T 11/006; G06T 2211/416; G06T 7/12; G06T 2207/10108; G06T 2207/30048; G06T 5/50; G06T 2207/20212; G06T 2211/428; G06T 2207/10104; G06T 7/73; G06T 7/0014; G06T 7/0016; G06T 7/254; G06T 7/0012; G06T 11/003; G06T 7/20; G06T 2207/10081; G06T 2207/20021; G06T 2211/412; G06T 2207/30028; G06T 12/20; G06T 12/30; G16H 50/30; G05D 1/0094; B64U 10/14; B64U 2101/30; B64U 2201/102

USPC ........................................................ 378/1, 62

See application file for complete search history.

(56) References Cited

U.S. PATENT DOCUMENTS

| | | | | |
|---|---|---|---|---|
| 6,177,675 | B1 * | 1/2001 | Gagnon | G01T 1/1647 250/369 |
| 7,467,008 | B2 | 12/2008 | Vija | |
| 7,723,689 | B2 | 5/2010 | Vija | |
| 7,759,646 | B2 | 7/2010 | Amemiya et al. | |
| 8,294,109 | B2 | 10/2012 | Vija | |
| 9,986,960 | B2 | 6/2018 | Ay et al. | |
| 10,772,582 | B2 | 9/2020 | Vija | |
| 11,439,358 | B2 | 9/2022 | Quinlan et al. | |
| 2007/0238950 | A1 | 10/2007 | Vija et al. | |
| 2008/0240343 | A1 | 10/2008 | Jabri et al. | |
| 2010/0172472 | A1 | 7/2010 | Ermes et al. | |
| 2011/0096970 | A1 | 4/2011 | Vija | |
| 2017/0007193 | A1 | 1/2017 | Nagler et al. | |
| 2018/0174293 | A1 | 6/2018 | Jin et al. | |
| 2021/0259652 | A1 | 8/2021 | Vija et al. | |

FOREIGN PATENT DOCUMENTS

| | | |
|---|---|---|
| JP | 2010500146 | 1/2010 |
| WO | 2020210532 | 10/2020 |

OTHER PUBLICATIONS

Zannoni, Elena Maria et al., "Intraoperative C-arm SPECT for hybrid operating room: A design study", The Journal of Nuclear Medicine (JNM), May 2019, 60 (supplement 1), 316, downloaded Aug. 3, 2021, retrieved from URL:https://jnm.snmjournals.org/content/60/supplement_1/316, (pp. 1-4, 4 total pages).

International Search Report for corresponding application No. PCT/US2021/072656, dated Feb. 16, 2022.

* cited by examiner

SMALL FOOTPRINT MULTI-USE SPECT SYSTEM

BACKGROUND

Conventional medical images may be generated via transmission imaging or emission imaging. In transmission imaging, the imaging source (e.g., an X-ray source) is external to the subject and the source radiation (e.g., X-rays) is transmitted through the subject to a detector. According to emission imaging, the imaging source (e.g., a gamma ray-emitting radiopharmaceutical) is internal to the subject (e.g., due to injection or ingestion thereof) and the source radiation (e.g., gamma rays) is emitted from within the subject to a detector.

Single-photon-emission-computed-tomography (SPECT) imaging is a type of emission imaging in which a gamma camera acquires planar projection images from several angular positions around a subject. The planar projection images must be acquired from a number and range of angular positions sufficient to tomographically reconstruct a three-dimensional image of the subject therefrom. Conventionally, the planar projection images are acquired by placing the subject into or near a gantry to which the gamma camera is attached and rotating the gantry so as to move the gamma camera to each desired angular position. Other systems attach a gamma camera to a mobile arm which is controlled to move the gamma camera to each angular position.

Both of the above-described SPECT systems require the area surrounding the object to be obstruction free, so that the gamma camera may move freely between the imaging positions which surround the subject. This requirement may be difficult to satisfy in many diagnostic and treatment settings, resulting in collisions which increase imaging time and may damage equipment or injure the subject. Moreover, a gantry-based system typically requires a large dedicated space into which the gantry is permanently mounted. Furthermore, since tomographic reconstruction requires acquisition of the planar projections from positions which surround the imaging subject, the size of the subject is limited to the volume circumscribed by the largest path over which the gamma camera may travel via the rotating gantry or the moveable arm.

Tomographic images may be acquired to facilitate diagnosis and/or treatment planning. Such diagnosis and/or treatment planning may include identifying a region of interest in a first tomographic image and determining to generate a second tomographic image centered on the region of interest. Since generation of the first tomographic image requires a first set of planar projection images and generation of the second tomographic image requires acquisition of a second set of planar projection images, this process may be unsuitably resource and time-consuming.

SPECT imaging systems which address one or more of the foregoing deficiencies are desired.

DETAILED DESCRIPTION

The following description is provided to enable any person in the art to make and use the described embodiments and sets forth the best mode contemplated for carrying out the described embodiments. Various modifications, however, will remain apparent to those in the art.

Some embodiments provide efficient generation and/or use of tomographic images. For example, a depth-resolving gamma camera may acquire a first tomographic image of a subject while the gamma camera is disposed at a single position with respect to the subject. Next, the gamma camera is moved to a second position with respect to the subject and acquires a tomographic image while disposed in the second position. Both the first tomographic image and the second tomographic image may depict one or more identical structures within the subject, albeit from different perspectives and/or distances. Embodiments may include combining, or "stitching" the first tomographic image and the second tomographic image together in view of consistency constraints imposed by identification of these identical structures. Additional tomographic images may be acquired and similarly combined with the combined tomographic image, again with respect to consistency constraints defined by structures common to the tomographic images to be combined. Some embodiments may thereby, for example, acquire a tomographic image of an object which is too large to be imaged using conventional methods.

Some embodiments may further or alternatively include acquisition of a first tomographic image of a subject while the gamma camera is disposed at a single position with respect to the subject, and use of the first tomographic image to determine a position from which a second tomographic image should be acquired. The gamma camera may then be moved to the second position to acquire a second tomographic image while disposed in the second position. In some embodiments, the gamma camera remains in the first position long enough to obtain a sufficient number of counts (i.e., qualifying gamma ray events) to generate a tomographic image suitable for enabling determination of the second position and remains in the second position for a longer period of time in order to obtain enough counts to generate a higher-quality tomographic image suitable for an intended analysis.

Figure 1A:
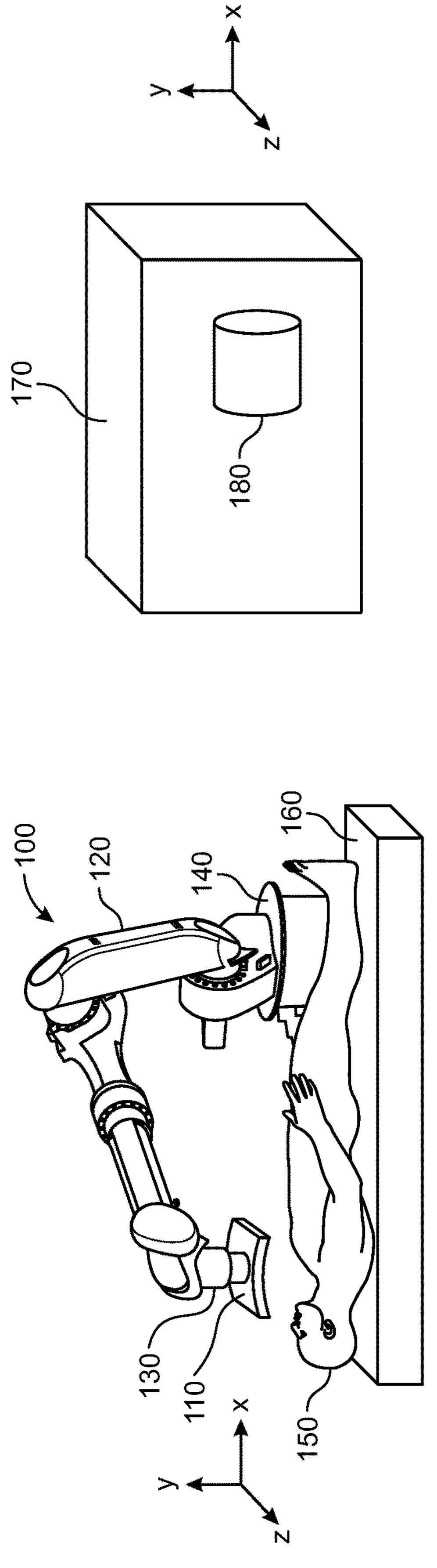
FIG. 1A illustrates a first detector position and a tomographic image acquired at the first detector position according to some embodiments.

FIG. 1A illustrates SPECT imaging system 100 according to some embodiments. As shown, SPECT imaging system 100 includes detector 110 connected to arm 120 via articulated coupling 130. Arm 120 is mounted to base 140, which may be fixed or mobile. Arm 120 may include one or more joints and may rotate or bend at each joint through various ranges of motion.

Bed 160 supports imaging subject 150 and may be movable to place subject 150 in a desired position with respect to detector 110. The desired position may be a position intended to best capture emission data emitted by a radioisotope located within a specific portion of subject 150. Generally, base 140, arm 120, coupling 130 and bed 160 may include any features and employ and mechanisms needed to facilitate selective positioning of detector 110 with respect to an imaging subject disposed on bed 160. Embodiments are not limited to the description or depiction of imaging system 100 provided herein.

Detector 110 may comprise any gamma ray detector that is or becomes known. Detector 110 is suitable generating a tomographic image from a fixed detector position, and embodiments include any image forming hardware and/or software technology for doing so. Current examples of such systems include a parallel hole collimator, a rotating acceptance angle collimator in which the aperture passageways in the collimator are arranged so that the angle of view of each row varies with respect to a radiation source, and a rotating slat collimator used in combination with a gamma camera having a scintillation detector formed of a stack of scintillation bar detectors. A rotating slat collimator collimates each of the bar detectors to receive gamma photons in only a single dimension. The scintillation bar detectors and collimator can be rotated to obtain event data from a subject at a number of azimuth angles of the rotating device.

Three-dimensional image 170 may be acquired by imaging system 100 while detector 110 is disposed at the position shown in FIG. 1A. Generally, image 170 includes depth information (i.e., in the y-direction) as well as (x, z) coordinates for events detected by detector 110. Image 170 may be generated by applying any suitable tomographic reconstruction algorithm to the event data acquired by detector 110 at the position shown in FIG. 1A.

As shown, image 170 depicts internal structure 180. Image 170 may depict other structures and structure 180 is illustrated for purposes of example. Image 170 may be grayscale or include colored pixels.

Figure 1B:
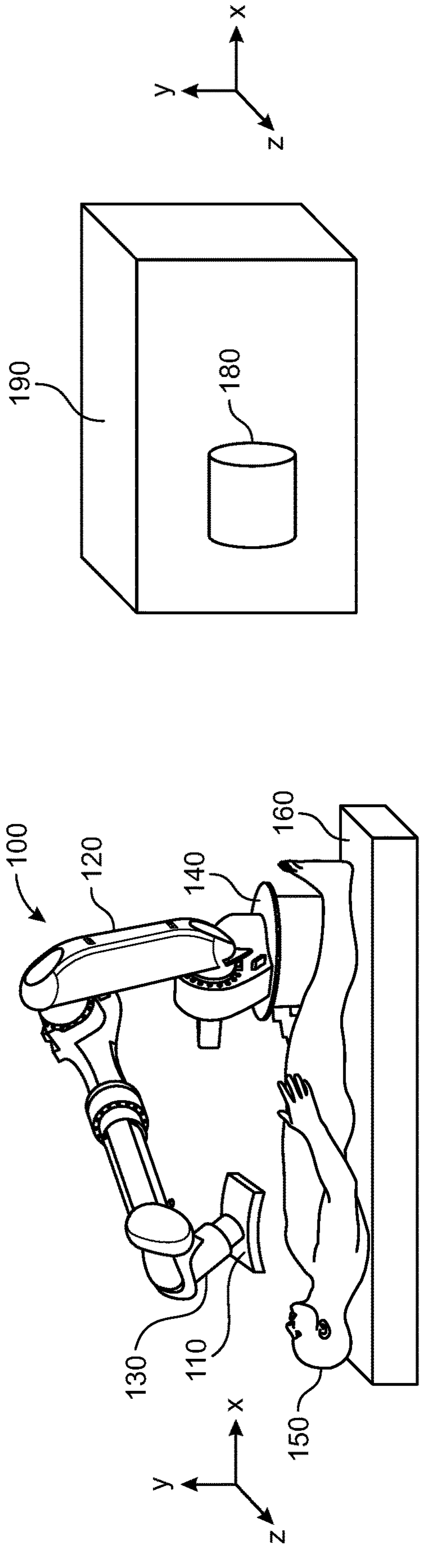
FIG. 1B illustrates a second detector position and a tomographic image acquired at the second detector position according to some embodiments.

FIG. 1B depicts imaging system 100 and shows detector 110 disposed in a position with respect to subject 150 which is different from the position shown in FIG. 1A. Arm 120 has moved so as to move detector 110 to the different position. For purposes of example, it will be assumed that detector 110 has moved in the x-direction. Accordingly, the first position and the second position are co-planar.

It will also be assumed that a second tomographic image is acquired while detector 110 is at the position of FIG. 1B. The second tomographic image is acquired based on events detected by detector 110 while disposed at the position.

Image 190 represents a tomographic image acquired based on the arrangement of FIG. 1B. Image 190 also depicts internal structure 180. Since subject 150 has remained stationary but detector 110 was moved from the position used to acquire image 170 in order to acquire image 190, internal structure 180 is disposed at a different position within image 190 as compared to image 170.

Figure 2:
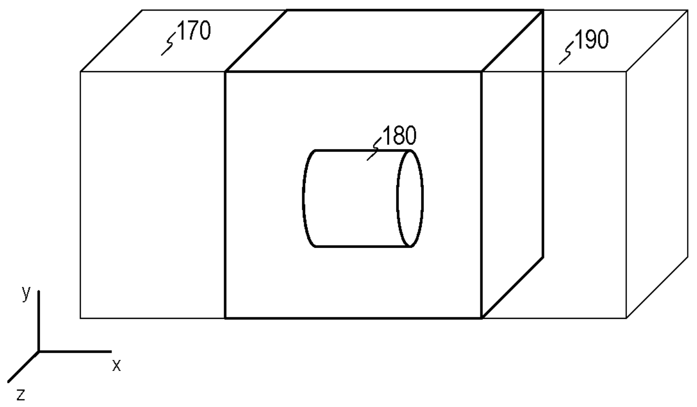
FIG. 2 illustrates stitching together of two tomographic images acquired at different detector positions according to some embodiments.

FIG. 2 illustrates combination of image 170 and image 190 according to some embodiments. According to some embodiments, image 170 and image 190 are combined by aligning pixels of image 170 which represent structure 180 with corresponding pixels of image 190 which represent structure 180. Combination of images 170 and 190 may also consider the relative positions of detector 110 during acquisition of the images. These relative images may be tracked via cameras disposed around system 100, sensors within detector 110 and/or sensors within arm 120, for example.

The combined image of FIG. 2 depicts a larger volume of subject 150 than is depicted by either image 170 or image 190. Embodiments may generate a combined image of any size, depending on the relative range of motion of detector 110.

Figure 3:
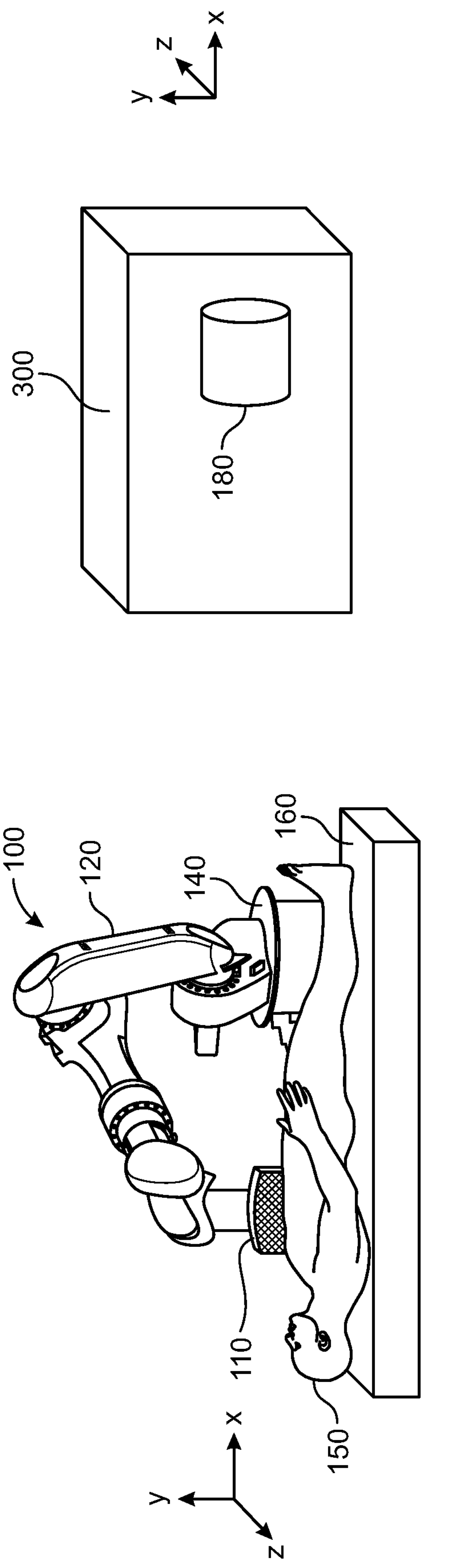
FIG. 3 illustrates a third detector position and a tomographic image acquired at the third detector position according to some embodiments.

FIG. 3 shows detector 110 in yet another position relative to subject 150. It will be assumed that tomographic image 300 is generated based on events detected by detector 110 while detector 110 is disposed in the position of FIG. 3. Image 300 also depicts structure 180.

Figure 4:
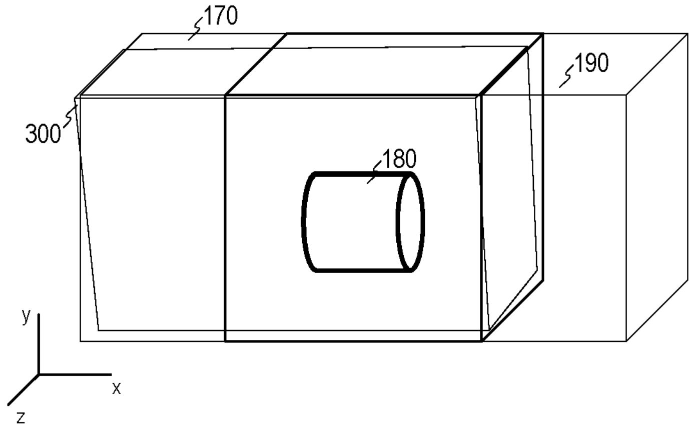
FIG. 4 illustrates stitching together of three tomographic images acquired at different detector positions according to some embodiments.

Accordingly, based on the pixels associated with structure 180, image 300 may be combined with image 170 and image 190 as shown in FIG. 4. The darker lines of FIG. 4 are intended to indicate that volumes which are depicted by two or more of the constituent tomographic images may be sharper than other volumes because they may be based on more event data than the other volumes. The sharpness of any of the constituent images may be controlled by increasing the amount of time during which detector 110 detects events used to generate the constituent image.

Figure 5:
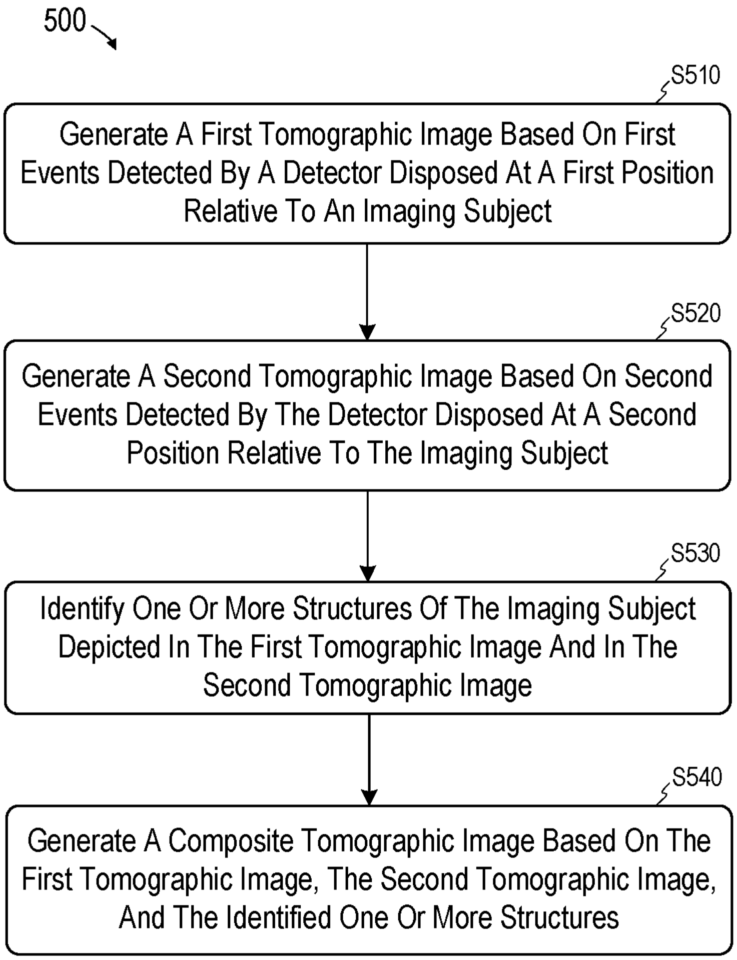
FIG. 5 is a flow diagram of a process to generate a composite tomographic image according to some embodiments.

FIG. 5 is a flow diagram of a process according to some embodiments. Process 500 and the other processes described herein may be performed using any suitable combination of hardware and software. Processor-executable program code embodying these processes may be stored by any non-transitory tangible medium, including a fixed disk, a volatile or non-volatile random access memory, a DVD, a Flash drive, or a magnetic tape. Embodiments are not limited to the examples described below.

Prior to process 500, an imaging subject (e.g., a human patient) is positioned on a support such as a bed. A radionuclide is introduced into the subject, for example via ingestion or injection, and a certain time period is allowed to pass in order to ensure that the radionuclide has reached a desired volume of the subject.

A detector is positioned at a first position relative to the imaging subject. Positioning of the detector may include moving an imaging base adjacent to the imaging subject and controlling an arm mounted to the based to move a detector mounted to the arm to the first position. At S510, a first tomographic image is acquired based on first events detected by the detector while disposed at the first position. As mentioned above, and image forming and tomographic reconstruction systems may be employed at S510 to generate the first tomographic image.

Next, the detector is positioned at a second position relative to the imaging subject. For example, the arm may be controlled while the base remains stationary to move the detector to the second position. A second tomographic image is then acquired at S520 based on second events detected by the detector while disposed at the second position.

At S530, one or more structures of the imaging subject which are depicted in both the first tomographic image and the second tomographic image are identified. The second position may be a position at which the detector is expected to receive gamma rays from at least a portion of the volume from which gamma rays were received by the detector when disposed at the first position. Such positioning may assist in ensuring that the second tomographic image depicts one or more structures which is also depicted in the first tomographic image.

The identification at S530 may comprise any image matching algorithms that are or become known, and may take into account the relative spatial difference between the first position and the second position. For example, if it is known that the second position reflects a lateral translation in one direction with respect to the first position, then the matching algorithm may linearly translate one of the tomographic images in the direction to facilitate the matching. Similar logic may account for rotational differences in the two positions.

A composite image is generated at S540. The composite image is generated based on the first tomographic image, the second tomographic image and the identified one or more structures. In one example, the first tomographic image and the second tomographic image are aligned with one another in order to best fit the pixels of the first tomographic image which depict the one or more structures with the pixels of the second tomographic image which depict the one or more structures. As described above, any number of tomographic images may be acquired at different positions and used to generate a composite tomographic image at S540 according to some embodiments. Each constituent tomographic image of the composite tomographic image may depict one or more structures which are depicted in at least one of the other constituent tomographic images, but embodiments are not limited thereto.

Figure 6:
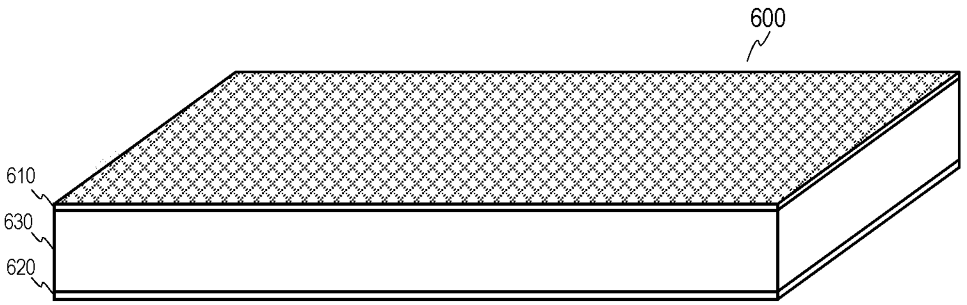
FIG. 6 is a view of a direct converter detector sensor array according to some embodiments.

A detector as described herein may comprise, but is not limited to, a direct converter detector as is known in the art. FIG. 6 is schematic depiction of components of a direct converter detector according to some embodiments. Detector 600 includes sensor array 610, cathode 620, and direct conversion material 630 therebetween. Sensor array 610 may comprise an array grid of hexagonal or otherwise-shaped sensors. In this regard, a sensor may also be referred to as an anode, a pixel or an electrode in the art.

Each of the sensors of sensor array 610 is coupled to a dedicated signal line and is not in direct electrical contact with its adjacent neighboring sensors. Cathode 620 may comprise a continuous layer which is generally transparent to gamma rays of energies that are to be detected by detector 600. Direct conversion material 630 may be composed of a single-crystal semiconductor material, such as CZT or Cadmium Telluride (CdTe).

Figure 7:
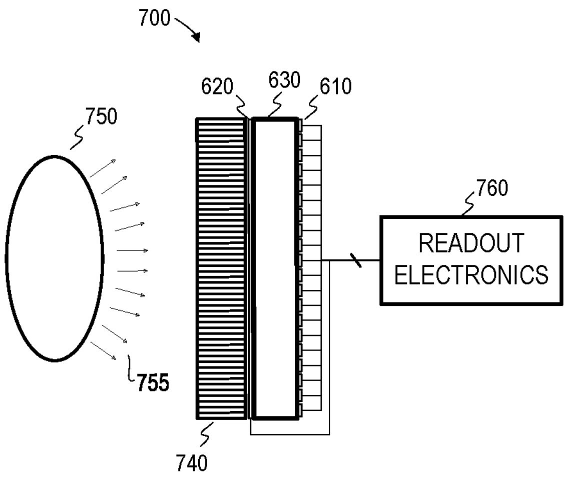
FIG. 7 illustrates imaging components according to some embodiments.

FIG. 7 is a schematic depiction of components of an imaging system during operation according to some embodiments. Detector 700 may implement the structure of detector 600, including sensor array 610, cathode 620, and direct conversion material 630 and as described above. Also shown is collimator 740 adjacent to cathode 620. Collimator 740 may comprise a multi-focal cone-beam collimator or parallel-hole collimator as is known in the art.

Detector 700 is positioned to detect gamma rays 755 emitted from volume 750. Certain ones of gamma rays 755 are collimated by collimator 740 to define their line-of-response and to filter out scattered or stray gamma radiation, and the thus-collimated gamma rays pass through cathode 620 due to its transparency thereto. A gamma ray penetrates into direct conversion material 630 and interacts with direct conversion material 630 to generate electron-hole pairs. Cathode 620 is held at a negative bias potential while the sensors of array 610 are held at a less-repelling potential. Consequently, the positively-charged holes drift towards cathode 620, while the negatively-charged electrons drift towards the sensors of array 610. As the electrons approach a given sensor of array 610, a signal is induced at the given sensor and at its neighboring sensors.

After collection of the electrons by the given sensor, readout electronics 760 may use the signals received from the neighboring sensors to determine a sub-pixel position of the given sensor at which the gamma ray will be assumed to have been received. The sub-pixel positions at which all gamma rays are received may then be used to generate a tomographic image of volume 750 as is known in the art.

Figure 8A:
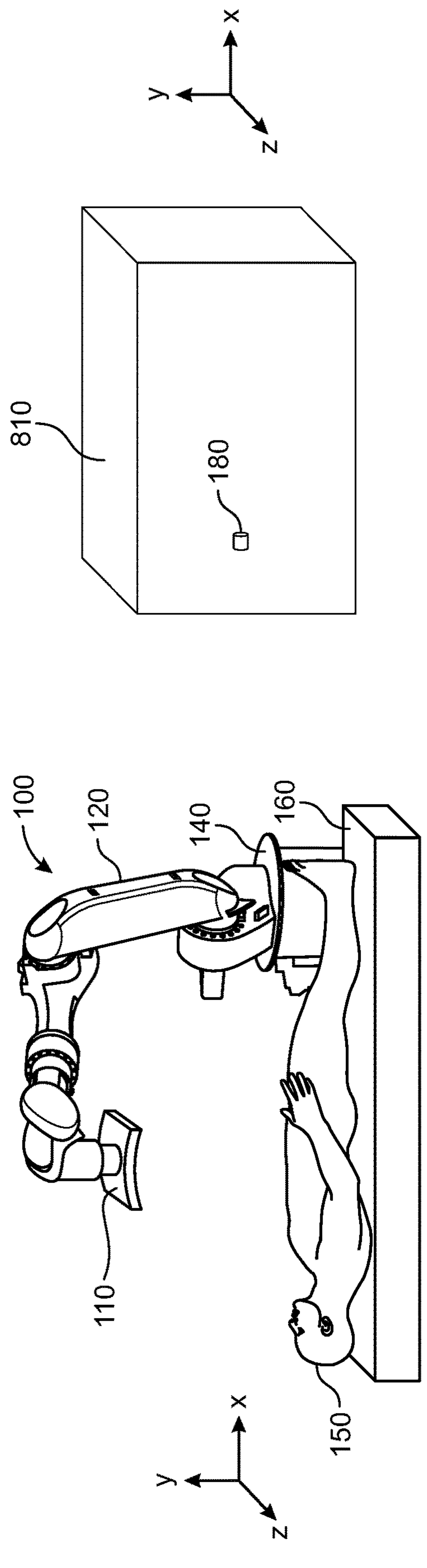
FIG. 8A illustrates a far view detector position and a tomographic image acquired at the far view detector position according to some embodiments.

FIG. 8A illustrates SPECT imaging system 100 according to some embodiments. It will be assumed that detector 100 is positioned as shown in FIG. 8A in order to acquire a tomographic image of a larger portion of subject 150 than that depicted in above-described images 170, 190 and 300. The image may be intended for use as a "scout" image which is used to identify a region of interest within subject 150. Accordingly, the acquisition time may be limited to only that required to generate a tomographic image suitable for identifying the region of interest. Such an image may be of relatively poor quality but the time required for its acquisition may advantageously be less than prior systems.

Three-dimensional image 810 is acquired by imaging system 100 while detector 110 is disposed at the position shown in FIG. 8A. Image 810 depicts internal structure 180 as mentioned above. However, since detector 110 is positioned farther from subject 150 in FIG. 8A than shown in FIGS. 1A, 1B and 3, internal structure 180 appears smaller and likely with less resolution in image 810 than in images 170, 190 and 300.

Figure 8B:
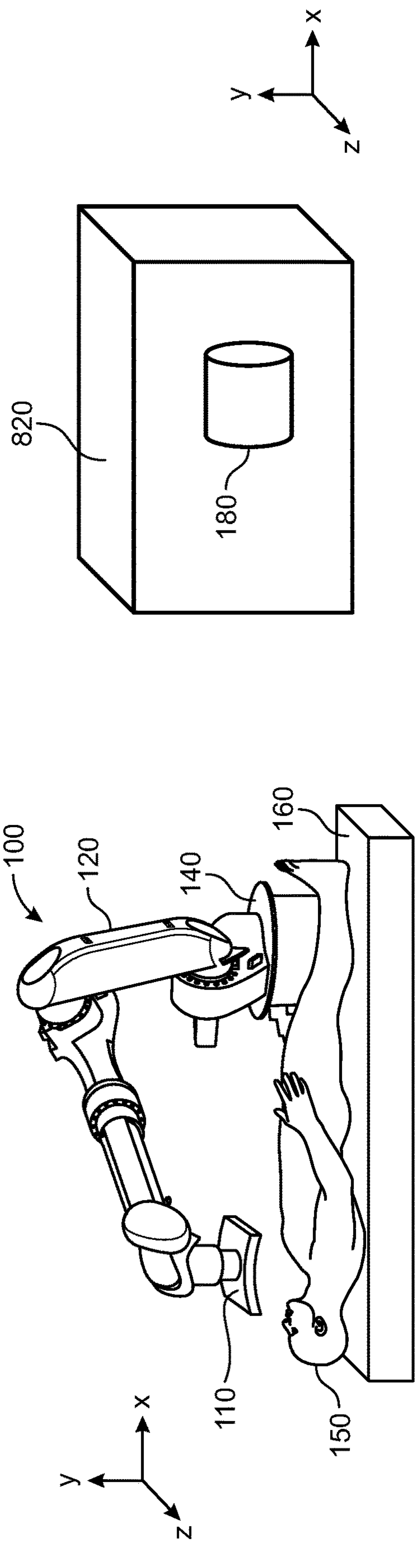
FIG. 8B illustrates a near view detector position and a tomographic image acquired at the near view detector position according to some embodiments.

Based on the identification of structure 180 and its location within image 810, detector 110 is moved to the position shown in FIG. 8B to acquire a more detailed tomographic image of structure 180. The position of detector 110 in FIG. 8B is closer to subject 150 than the position of detector 110 in FIG. 8A. At the position of FIG. 8A, a larger portion of the subject 150 is within a subtended angle from which detector receives gamma rays than at the position of FIG. 8B.

The acquired image is shown as image 820 of FIG. 8B. Structure 180 appears larger than in image 810 of FIG. 8A. Moreover, an acquisition period over which data used to generate image 820 was acquired may be longer than that used to acquire the data of image 810, in order to result in a higher-resolution image than image 810 (denoted by the heavier lines of image 820).

Figure 9:
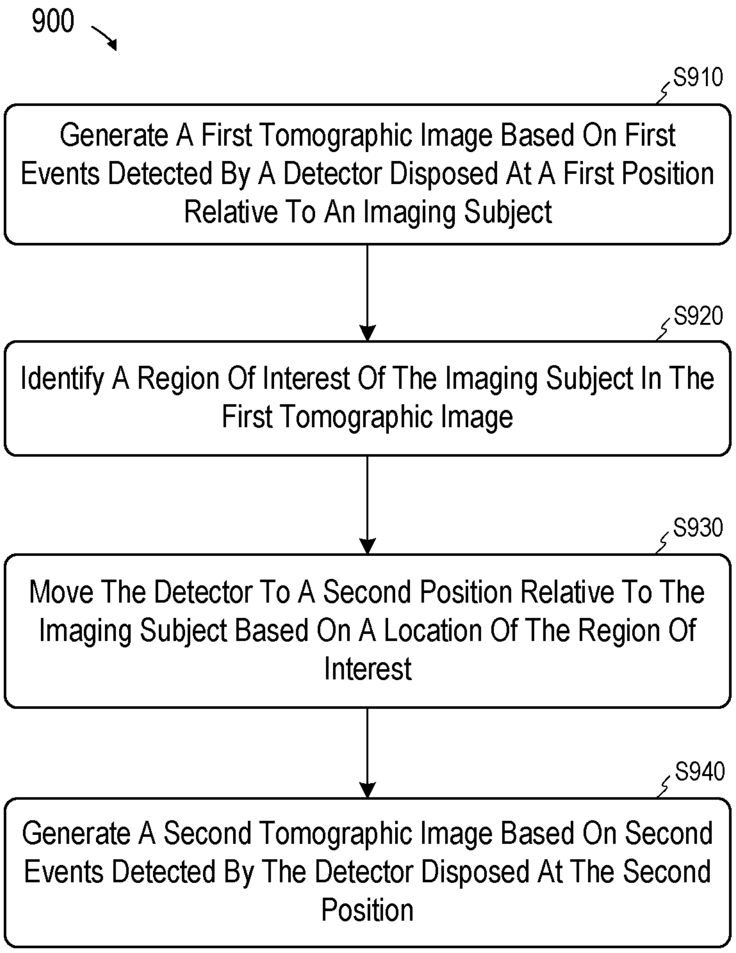
FIG. 9 is a flow diagram of a process to acquire tomographic images according to some embodiments.

FIG. 9 is a flow diagram of process 900 according to some embodiments. It will again be assumed that, prior to process 500, an imaging subject (e.g., a human patient) is positioned on a support such as a bed and a radionuclide is introduced into the imaging subject. A SPECT detector as described herein is moved to a first position relative to the imaging subject. As described above, the first position may be a position at which emissions from a large portion of the imaging subject are expected to be received, thereby enabling generation of a tomographic image of the large portion.

At S910, a first tomographic image is acquired based on first events detected by the detector while disposed at the first position. The first tomographic image may be acquired using any image formation system and/or reconstruction algorithm that is or becomes known. A region of interest of the imaging subject is identified at S920 within the first tomographic image, and the detector is moved to a second position relative to the imaging subject based on a location of the region of interest.

S920 and S930 may comprise displaying the first tomographic image to an operator, who identifies a region of interest (e.g., a heart) and controls a detector arm to position the detector adjacent to a particular surface of the heart. The identification at S920 and movement at S930 may be performed automatically based on a pre-defined target organ or structure. The first tomographic image may be automatically segmented to identify different regions within the imaging subject, and the segmented image may be displayed to an operator for identification of the region of interest. Once the operator identifies the region of interest (and. for example, a desired view perspective) based on the segmented image, the imaging system may automatically move the detector to the second position based on the location of the region of interest.

At S940, a second tomographic image is acquired based on second events detected by the detector while disposed at the second position. The second tomographic image may provide more information regarding the region of interest than the first tomographic image. The acquisition time of the second tomographic image may be greater than the acquisition time of the first tomographic image in order to provide a suitable-quality image of the region of interest.

Figure 10A:
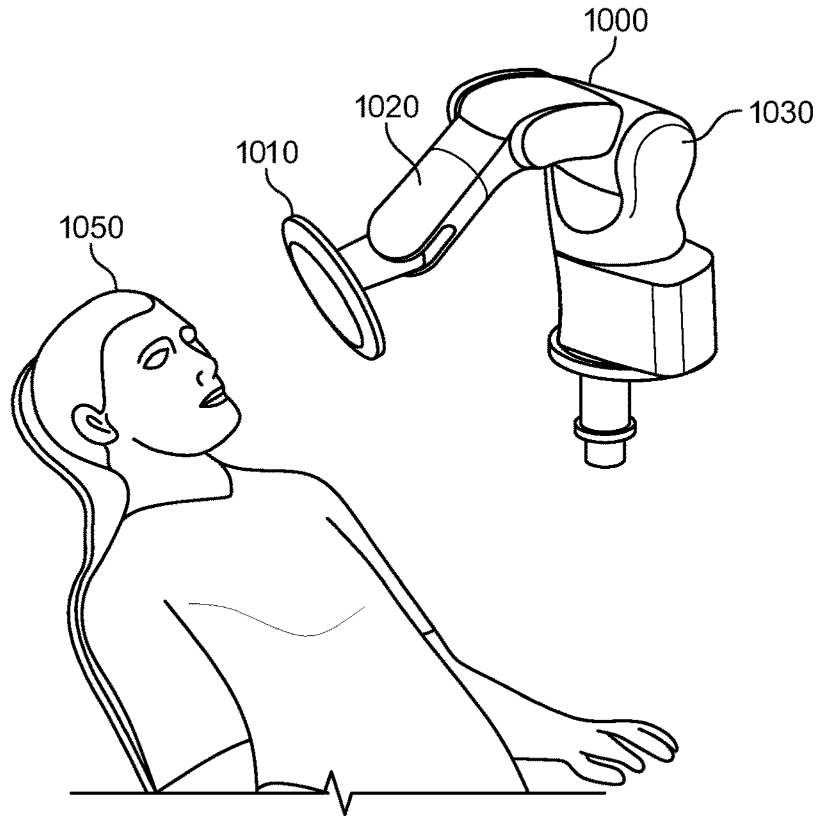
FIG. 10A illustrates acquisition of a tomographic image at a first detector position according to some embodiments.
Figure 10B:
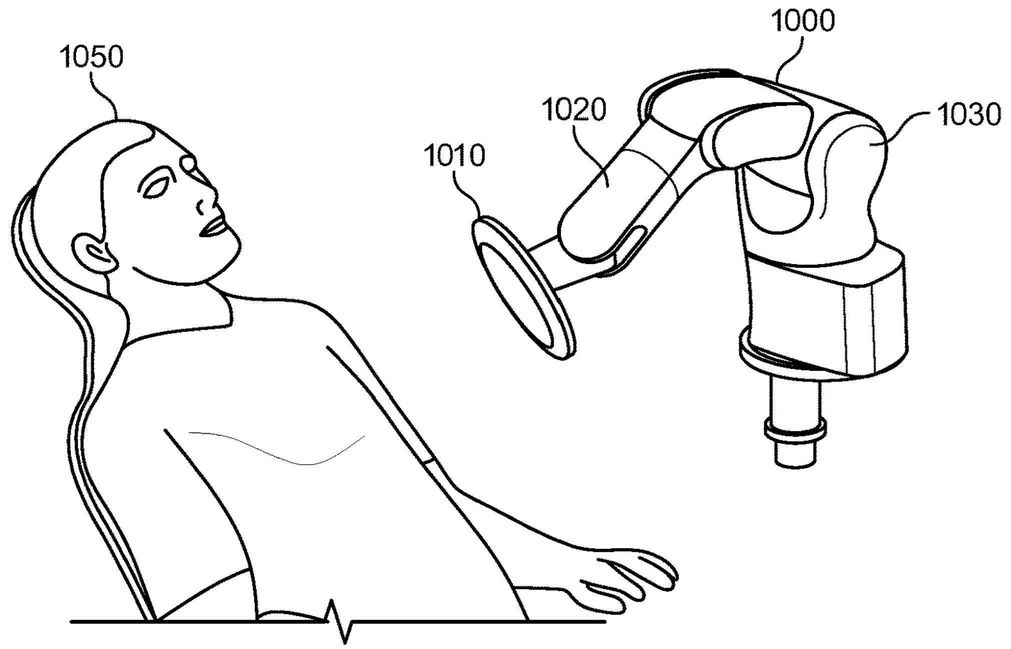
FIG. 10B illustrates acquisition of a tomographic image at a second detector position according to some embodiments.

FIGS. 10A and 10B illustrate imaging system 1000 and imaging subject 1050 according to some embodiments. Imaging system 1000 includes detector 1010 coupled to articulated arm 1020. Arm 1020 is coupled to base interface 1030 which may, in some embodiments, interface with one or more different types of mobile and/or stationary bases (not shown). Base interface includes components necessary to carry control and data signals between detector 1010, arm 1020 and a base (which is in turn coupled to a control system (not shown)).

FIG. 10A shows detector 1010 disposed at a first position with respect to subject 1050. It will be assumed that detector 1010 acquires a first tomographic image while disposed at the first position. In FIG. 10B, detector 1010 is disposed at a second position with respect to subject 1050. Detector 1010 acquires a second tomographic image while disposed at the second position, and the first and second tomographic images may thereafter be combined into a composite tomographic image as described above. Moreover, the second position may have been determined based on identification of a region of interest within the first tomographic image, as also described above.

Figure 11:
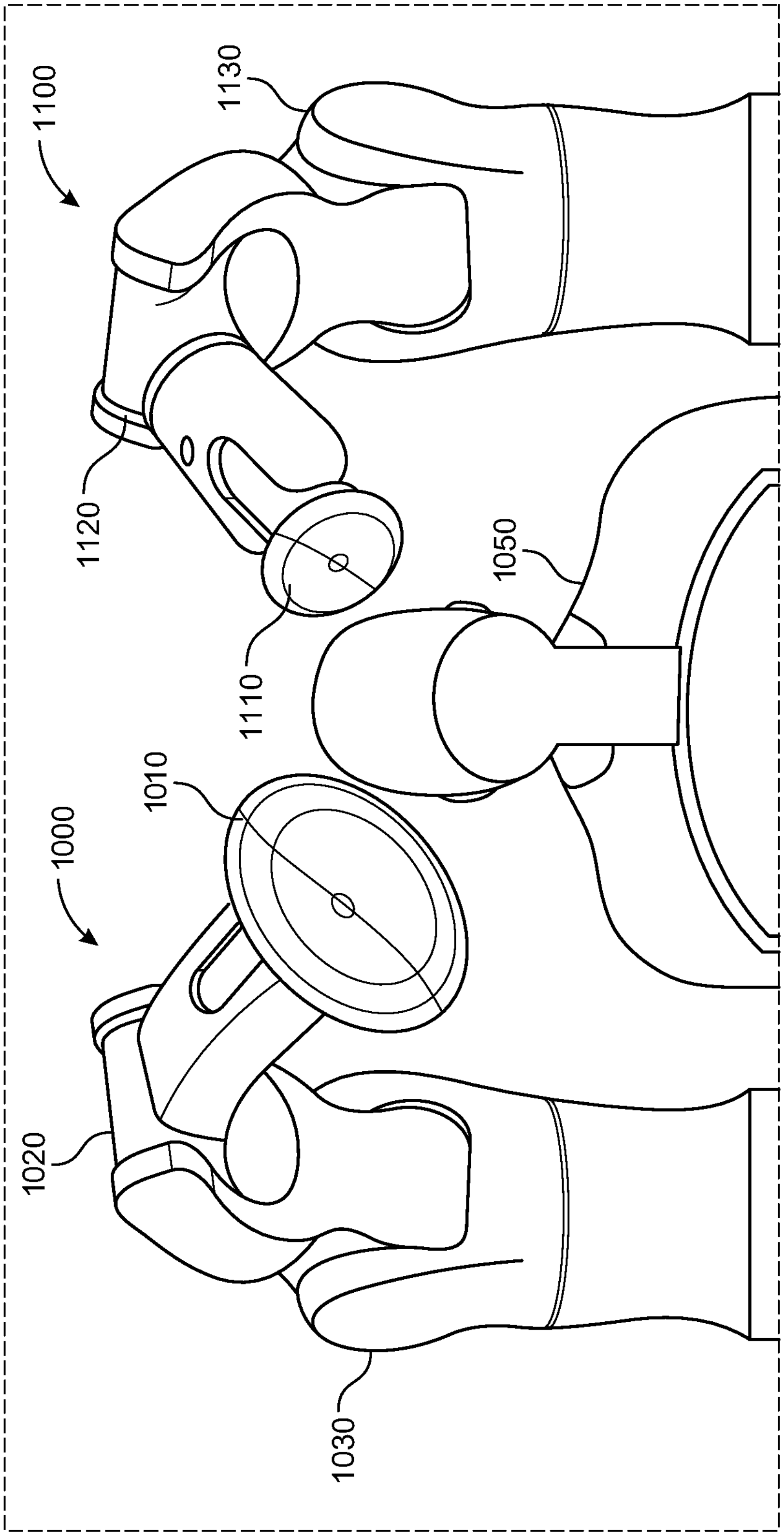
FIG. 11 illustrates acquisition of two tomographic images by two detectors according to some embodiments.

FIG. 11 illustrates imaging system 1000 and subject 1050 as described above. Also illustrated is imaging system 1100 including detector 1110 coupled to articulated arm 1120 which is in turn coupled to base 1130. The components of imaging system 1100 may differ from the components of imaging system 1000.

Detector 1010 of FIG. 11 is disposed at a first position with respect to subject 1050, while detector 1110 is disposed at a second position with respect to subject 1050. Detector 1010 may acquire a first tomographic image while disposed at the first position and detector 1110 may acquire a second tomographic image while disposed at the second position. These first and second tomographic images may be combined into a composite tomographic image based on one or more structures depicted in both tomographic images, as described above.

Figure 12A:
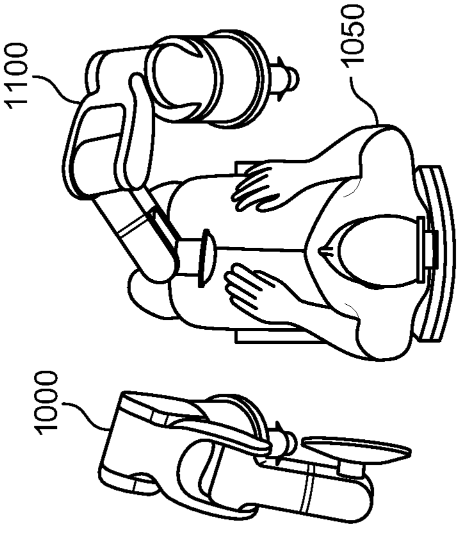
FIGS. 12A through 12C each illustrate acquisition of two tomographic images by two detectors according to some embodiments.
Figure 12B:
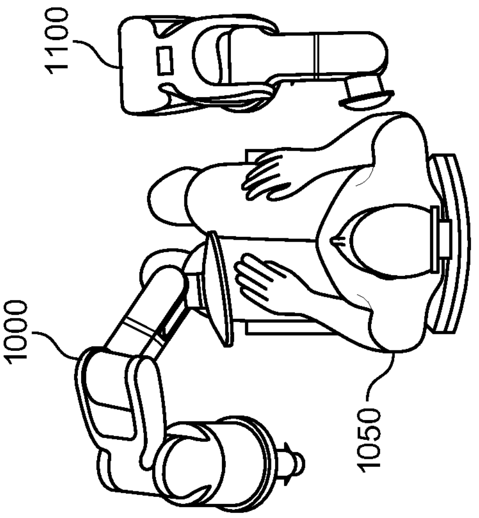
Figure 12C:
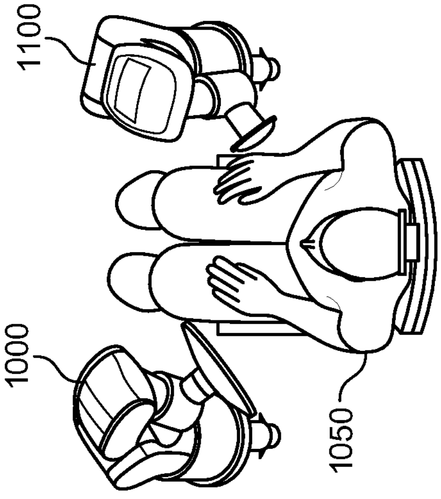

FIGS. 12A through 12C illustrate detectors 1010 and 1110 of imaging systems 1000 and 1100 at different positions with respect to subject 1050. Tomographic images acquired by each detector while disposed at any or all the depicted positions may be combined into a composite image as described above. Moreover, a tomographic image acquired by one of detectors 1010 and 1110 may be used to identify a region of interest and determine a second position from which either detector 1010 or 1110 is to acquire a next tomographic image.

Figure 13:
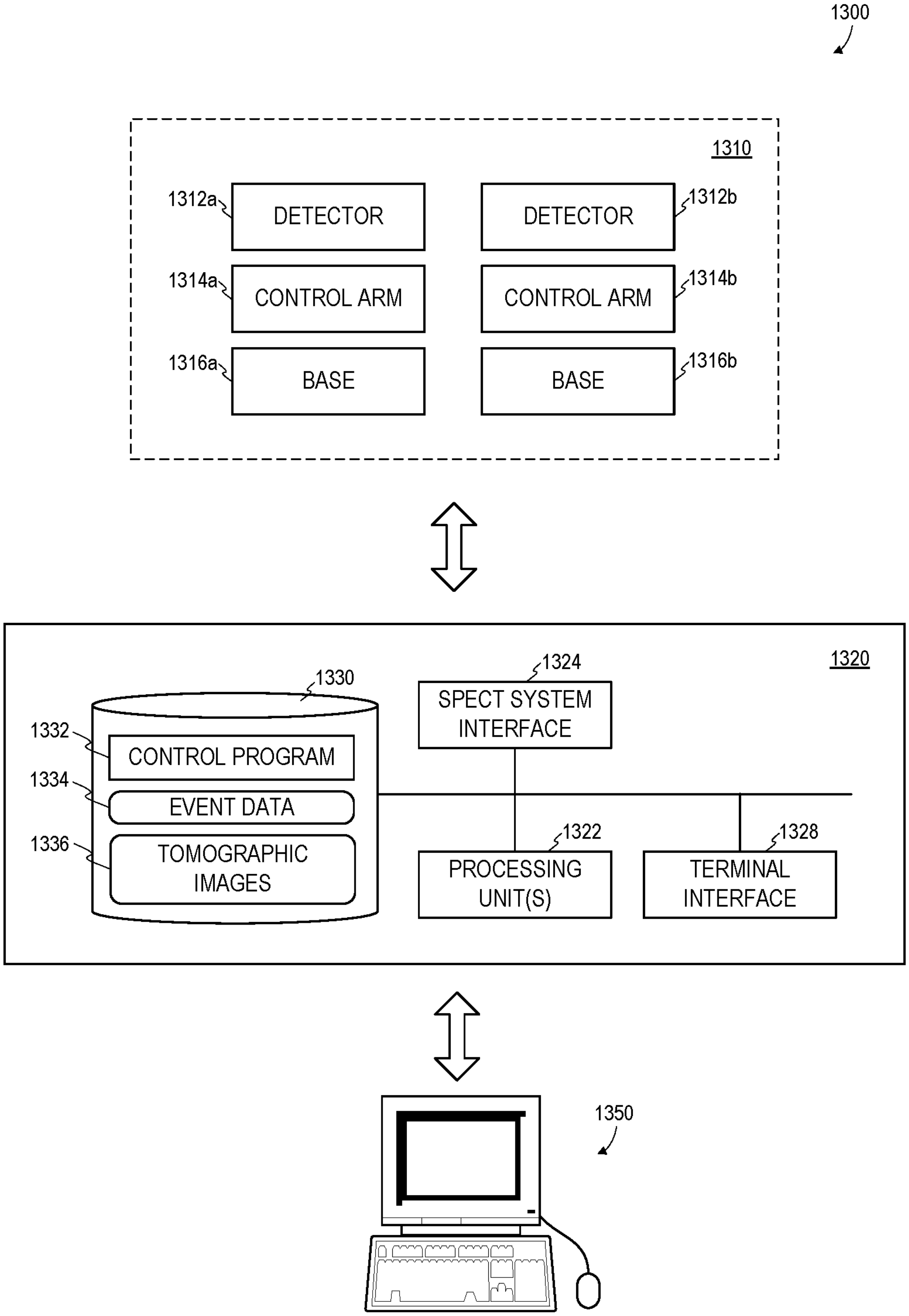
FIG. 13 illustrates components of a SPECT imaging system according to some embodiments.

FIG. 13 illustrates SPECT imaging system 1300 according to some embodiments. System 1300 includes imaging hardware 1310 which, in the illustrated embodiment, includes two detectors 1312*a*, 1312*b* and associated control arms 1314*a*, 1314*b* and bases 1316*a*, 1316*b*. Embodiments are not limited to or required to include two independent detectors/arms/bases.

Control system 1320 sends and receives control signals and data to and from imaging hardware 1310. Control system 1320 may comprise any general-purpose or dedicated computing system. Control system 1320 includes one or more processing units 1322 configured to execute processor-executable program code to cause system 1320 to operate as described herein, and storage device 1330 for storing the program code. Storage device 1330 may comprise one or more fixed disks, solid-state random access memory, and/or removable media (e.g., a thumb drive) mounted in a corresponding interface (e.g., a USB port).

Storage device 1330 stores program code of system control program 1332. One or more processing units 1322 may execute system control program 1332, in conjunction with SPECT system interface 1324, to control motors, servos, and encoders to cause control arms 1314*a*, 1314*b* to move detectors 1312*a*, 1312*b* to desired positions, and to acquire event data 1334 at each position. The event data 1334 may be stored in memory 1330. Control program 1332 may also be executed to generate tomographic images 1336 from event data 1334 and to combine tomographic images 1336 as described herein.

Terminal 1350 may comprise a display device and an input device coupled to system 1320. Terminal 1350 may display tomographic images 1336 stored in memory 1330, and may receive operator input identifying a region of interest within a displayed tomographic image. In some embodiments, terminal 1350 is a separate computing device such as, but not limited to, a desktop computer, a laptop computer, a tablet computer, and a smartphone.

Each of component of system 1300 may include other elements which are necessary for the operation thereof, as well as additional elements for providing functions other than those described herein.

Each functional component described herein may be implemented at least in part in computer hardware, in program code and/or in one or more computing systems executing such program code as is known in the art. Such a computing system may include one or more processing units which execute processor-executable program code stored in a memory system.

The foregoing diagrams represent logical architectures for describing processes according to some embodiments, and actual implementations may include more or different components arranged in other manners. Other topologies may be used in conjunction with other embodiments. Moreover, each component or device described herein may be implemented by any number of devices in communication via any number of other public and/or private networks. Two or more of such computing devices may be located remote from one another and may communicate with one another via any known manner of network(s) and/or a dedicated connection. Each component or device may comprise any number of hardware and/or software elements suitable to provide the functions described herein as well as any other functions. For example, any computing device used in an implementation of a system according to some embodiments may include a processor to execute program code such that the computing device operates as described herein.

All systems and processes discussed herein may be embodied in program code stored on one or more non-transitory computer-readable media. Such media may include, for example, a hard disk, a DVD-ROM, a Flash drive, magnetic tape, and solid state Random Access Memory or Read Only Memory storage units. Embodiments are therefore not limited to any specific combination of hardware and software.

Those in the art will appreciate that various adaptations and modifications of the above-described embodiments can be configured without departing from the claims. Therefore, it is to be understood that the claims may be practiced other than as specifically described herein.

What is claimed is:

1. A system comprising:

a gamma ray detector; and a control system to:

generate a first tomographic image of a subject based on first gamma rays detected by the detector while the detector is disposed at a first position with respect to the subject;

generate a second tomographic image of the subject based on second gamma rays detected by the detector while the detector is disposed at a second position with respect to the subject;

identify one or more structures of the subject depicted in the first tomographic image and the second tomographic image; and generate a composite tomographic image by aligning first pixels of the first tomographic image depicting the identified one or more structures with second pixels of the second tomographic image depicting the identified one or more structures.

2. The system according to claim 1, the control system to:

generate a third tomographic image of the subject based on third gamma rays detected by the detector while the detector is disposed at a third position with respect to the subject;

identify a second one or more structures of the subject depicted in the composite tomographic image and the third tomographic image; and generate a second composite tomographic image based on the composite tomographic image, the third tomographic image, and the identified second one or more structures.

3. The system according to claim 2, wherein the first position and the second position are co-planar and the third position is not co-planar with the first position and the second position.

4. The system according to claim 3, wherein generation of the second composite tomographic image comprises aligning third pixels of the composite tomographic image depicting the second one or more structures with fourth pixels of the third tomographic image depicting the second one or more structures.

5. The system according to claim 1, wherein the first position and the second position are co-planar.

6. A method comprising:

generating a first tomographic image of a subject based on first gamma rays detected by a detector while the detector is disposed at a first position with respect to the subject;

generating a second tomographic image of the subject based on second gamma rays detected by the detector while the detector is disposed at a second position with respect to the subject;

identifying one or more structures of the subject depicted in the first tomographic image and the second tomographic image; and generating a composite tomographic image by aligning first pixels of the first tomographic image depicting the identified one or more structures with second pixels of the second tomographic image depicting the identified one or more structures.

7. The method according to claim 6, further comprising:

generating a third tomographic image of the subject based on third gamma rays detected by the detector while the detector is disposed at a third position with respect to the subject;

identifying a second one or more structures of the subject depicted in the composite tomographic image and the third tomographic image; and generating a second composite tomographic image based on the composite tomographic image, the third tomographic image, and the identified second one or more structures.

8. The method according to claim 7, wherein the first position and the second position are co-planar and the third position is not co-planar with the first position and the second position.

9. The method according to claim 8, wherein generating the second composite tomographic image comprises aligning third pixels of the composite tomographic image depicting the second one or more structures with fourth pixels of the third tomographic image depicting the second one or more structures.

10. The method according to claim 6, wherein the first position and the second position are co-planar.

11. A system comprising:

a gamma ray detector; and a control system to:

generate a first tomographic image of a subject based on first gamma rays detected by the detector while the detector is disposed at a first position with respect to the subject;

identify a region of interest within the first tomographic image;

determine a second detector position based on the region of interest;

move the detector to the second position; and generate a second tomographic image of the subject based on second gamma rays detected by the detector while the detector is disposed at the second position;

identify one or more structures of the subject depicted in the first tomographic image and the second tomographic image; and generate a composite tomographic image by aligning first pixels of the second tomographic image depicting the one or more structures with second pixels of the third tomographic image depicting the one or more structures.

12. The system according to claim 11, the control system to:

generate a third tomographic image of the subject based on third gamma rays detected by the detector while the detector is disposed at a third position with respect to the subject;

identify one or more structures of the subject depicted in the second tomographic image and the third tomographic image; and generate a composite tomographic image based on the second tomographic image, the third tomographic image, and the identified one or more structures.

13. The system according to claim 12, wherein the third position and the second position are co-planar and the first position is not co-planar with the third position and the second position.

14. The system according to claim 11, wherein the second detector position is closer to the subject than the first detector position.

15. The system according to claim 14, wherein a resolution of the second tomographic image is greater than a resolution of the first tomographic image.

16. The system according to claim 11, wherein a resolution of the second tomographic image is greater than a resolution of the first tomographic image.

* * * * *